(12) United States Patent
Miller

(10) Patent No.: US 10,285,922 B1
(45) Date of Patent: May 14, 2019

(54) TOPICAL EXFOLIATING FORMULATION

(71) Applicant: Bruce Wayne Miller, Naples, FL (US)

(72) Inventor: Bruce Wayne Miller, Naples, FL (US)

(*) Notice: Subject to any disclaimer, the term of this patent is extended or adjusted under 35 U.S.C. 154(b) by 0 days.

(21) Appl. No.: 16/256,034

(22) Filed: Jan. 24, 2019

(51) Int. Cl.
| | |
|---|---|
| *A61Q 19/10* | (2006.01) |
| *A61K 8/81* | (2006.01) |
| *A61K 8/44* | (2006.01) |
| *A61K 8/34* | (2006.01) |
| *A61K 8/891* | (2006.01) |
| *A61K 8/66* | (2006.01) |
| *A61K 8/9789* | (2017.01) |
| *A61K 8/41* | (2006.01) |

(52) U.S. Cl.
CPC ............. *A61K 8/8147* (2013.01); *A61K 8/34* (2013.01); *A61K 8/345* (2013.01); *A61K 8/416* (2013.01); *A61K 8/44* (2013.01); *A61K 8/66* (2013.01); *A61K 8/891* (2013.01); *A61K 8/9789* (2017.08); *A61Q 19/10* (2013.01); *A61K 2800/28* (2013.01); *A61K 2800/87* (2013.01)

(58) Field of Classification Search
CPC ................ A61K 8/416; A61K 2800/28; A61K 2800/87; A61Q 19/10
See application file for complete search history.

(56) References Cited

U.S. PATENT DOCUMENTS

| | | | | |
|---|---|---|---|---|
| 2,917,433 | A | * 12/1959 | Goldman | ........... A61K 38/4873 424/94.63 |
| 2010/0278906 | A1 | * 11/2010 | Sondgeroth | ............ A61K 8/416 424/450 |

* cited by examiner

*Primary Examiner* — Ernst V Arnold
(74) *Attorney, Agent, or Firm* — Tiffany C. Miller; Inventions International Inc.

(57) ABSTRACT

An aqueous formulation for topical chemical exfoliation to the skin containing purified water, polyacrylic acid, disodium ethylenediaminetetraacetate, glycerin, specially denatured alcohol, dimethicone, cetyltrimethylammonium chloride, papain enzyme, citrus seed extract, and a nontoxic preservative. The formulation may further contain benzylalcohol and dehydroacetic acid which serve as effective nontoxic preservatives. The exfoliating formulations of the invention are useful in the removal of the surface layer of the skin and in particular, the dead cells of the stratum corneum. The formulation may be retained in an air tight vessel such as a syringe. About 5 rads to about 10 rads of gamma radiation may be applied to the formulation retained within the air tight vessel.

24 Claims, No Drawings

TOPICAL EXFOLIATING FORMULATION

BACKGROUND OF THE INVENTION

1. Field of the Invention

This invention relates, generally, to topically applied pharmaceutical formulations for the removal of the surface layer of the skin and the dead cells of the stratum corneum. In particular, the invention pertains to the exfoliating formulations containing papain enzyme and preservatives such as benzylalcohol and dehydroacetic acid.

2. Background Art

The Food and Drug Administration does not regulate many of the chemicals used in the manufacture of cosmetics in today's market. This unregulated usage of toxic chemicals such as, parabens, lead, musks, formaldehyde, toluene, hydroquinone, triclosan, and phthalates, within cosmetics and personal care products has made unsuspecting consumers susceptible to harmful side effects including, but not limited to, cancer, birth defects, pregnancy complications, contact dermatitis, or hormone interruption. Thus, there is a need for the manufacture of a novel topical exfoliating formulation that contains nontoxic preservatives, nontoxic active ingredients, and nontoxic inactive ingredients, thereby, providing a user with a safe and effective topical exfoliating formulation.

Prior art topical exfoliating formulations remove the top layer of the skin with the use of microbeads. The problem with the use of microbeads as an exfoliating agent in cosmetics and personal care products is the environmental implications. For example, the plastic particles of the microbeads that have been washed down the drain pollute rivers and canals that they pass through. Further, many animals and freshwater fish exposed to this form of plastic particle water pollution may ingest the microbeads which result in adverse behavioral effects and potential for biological toxicity within the organism. The current regulations imposed on the use of microbeads within cosmetics and personal care products have facilitated the need to eliminate microbeads from exfoliating formulations in the U.S. market. What is therefore needed is a novel topical exfoliating formulation that is capable of removing the top layer of skin of a user without the use of including, but not limited to, microbeads, salt, sand, or sugar. As a result, the environmental pollution associated with the use of the novel topical exfoliating formulation has been reduced or eliminated.

Many chemicals used in the manufacture of topical exfoliating formulations have been contaminated with harmful microorganisms including, but not limited to, bacteria, mold, yeast, and fungus. For example, microbial contamination and occurrence of skin contamination due to these harmful microorganisms within the chemicals of a formulation may result in bacterial infections of a user including, but not limited to, *Staphylococcus Aureus, Pseudomonas Aeruginosa*, or *Escherichia Coli*. It would be more desirable to remove these contaminants from the novel topical exfoliating formulation during packaging of the product or prior to distribution of the product to the market. Thus, there is a need for microorganism decontamination with gamma irradiation processing using gamma sterilization technology to expose the novel topical exfoliating formulation and its packaging to gamma radiation. As a result, many harmful microorganisms may be reduced or even eliminated from the chemicals used in the novel topical exfoliating formulation.

Many packaging containers used to retain topical exfoliating formulations in today's market are jars having removable lids. The problem with dispensing a topical exfoliating formulation from a jar with a removable lid is that it requires a user to manually dip their finger into the jar to scoop out the product during use, thereby, cross contaminating the product with harmful microorganisms from a user to the product. It would be more desirable to dispense the novel topical exfoliating formulation from an airless pump syringe, thereby eliminating the cross contamination of microorganisms from a user to the product. As a result, the shelf life of the product will be increased and the user will be less susceptible to contracting a disease from microbial contamination during use of the novel topical exfoliating formulation.

However, in view of the prior art considered as a whole at the time the present invention was made, it was not obvious to those of ordinary skill in the pertinent art how the identified needs could be fulfilled.

DESCRIPTION OF THE INVENTION

The long-standing but heretofore unfulfilled need for an aqueous formulation for topical chemical exfoliation to the skin containing purified water, polyacrylic acid, disodium ethylenediaminetetraacetate chelating agent, glycerin, specially denatured alcohol, dimethicone, cetyltrimethylammonium chloride, citrus seed extract, and at least two nontoxic preservatives such as papain enzyme and benzylalcohol dehydroacetic acid. The exfoliating formulations of the invention are useful in the removal of the surface layer of the skin and in particular, the dead cells of the stratum corneum. The formulation may be retained in an air tight vessel such as an airless pump syringe. About 5 rads to about 10 rads of gamma radiation may be applied to the formulation retained within the air tight vessel. The novel topical exfoliating formulation also includes improvements that overcome the limitations of prior art exfoliating formulations and is now met by a new, useful, and non-obvious invention.

The following description is not to be construed as limiting. Numerous specific details are described to provide a thorough understanding of the invention. However, in certain instances, well know or conventional details are not described in order to avoid obscuring the description. References to one or an embodiment in the present disclosure are not necessarily references to the same embodiment; and, such references refer to at least one.

Reference in this specification to "a general embodiment" or "an alternate embodiment" means that a particular feature, structure, or characteristic described in connection with the embodiment is included in at least one embodiment of the disclosure. The appearances of the phrase "an alternate embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not for other embodiments.

In a general embodiment, the novel aqueous formulation for topical chemical exfoliation to the skin has by weight about 80.000% to about 90.000% water, about 3.000% to about 4.000% polyacrylic acid, about 0.025% to about 0.100% disodium ethylenediaminetetraacetate chelating agent, about 0.250% to about 1.000% glycerin, about 3.000% to about 5.000% specially denatured alcohol, about 0.025% to about 0.100% dimethicone, about 4.000% to about 6.000% cetyltrimethylammonium chloride, about 0.0001% to about 0.025% papain enzyme, about 0.025% to about 1.000% citrus seed extract, and about 0.025% to about 1.000% preservative.

It is within the scope of this invention for the novel topical exfoliating formulation to include about 86.139% water.

It is within the scope of this invention for the novel topical exfoliating formulation to be a gel and to include about 3.250% polyacrylic acid. The use of this carbomer as a rheology modifier provides an increase in viscosity and may provide the novel topical exfoliating formulation with the characteristics of a sparkling clear gel or a hydro-alcoholic gel. It is within the scope of this invention for the formulation to include polyacrylic acid being crosslinked with an allyl ether of including, but not limited to, pentaerythritol, sucrose, or propylene.

In a preferred embodiment, the novel topical exfoliating formulation has about 0.050% disodium ethylenediaminetetraacetate chelating agent. Ethylenediaminetetraacetic acid chelating agents are capable of controlling common multivalent metal ions by chemically binding and rendering inactive the associated trace metals having an adverse impact on characteristics of pharmaceuticals including, but not limited to, color, clarity, and shelf life. Disodium ethylenediaminetetraacetate chelating agent is considered a food preservative in the U.S. Food and Drug Administration regulations and may facilitate antimicrobial activity of the novel topical exfoliating formulation. In a preferred embodiment, the novel topical exfoliating formulation has about 0.050% disodium ethylenediaminetetraacetate chelating agent salt crystals.

In a preferred embodiment, the novel topical exfoliating formulation has about 0.500% glycerin. Glycerin is capable of improving smoothness, increasing lubrication, and preserving moisture of the novel topical exfoliating formulation.

In a preferred embodiment, the novel topical exfoliating formulation has about 4.000% specially denatured alcohol. It is a preferred embodiment for a specially denatured alcohol 40B having components of 200 proof Ethanol at 99.86% (v/v) and 0.14% (v/v) tert-Butyl alcohol and brucine sulfate. Further, it is within the scope of this invention for the specially denatured alcohol to be denatured with tert-Butyl alcohol. Specially denatured alcohol 40B is capable of functioning as including, but not limited to, an antifoaming agent, a solvent, an astringent, an antimicrobial agent of the novel topical exfoliating formulation.

In a preferred embodiment, the novel topical exfoliating formulation has about 0.050% dimethicone. In particular, SF 13-350 polydimethylsiloxane fluid may be used as an antifoam agent component of the novel topical exfoliating formulation.

In a preferred embodiment, the novel topical exfoliating formulation has about 5.000% cetyltrimethylammonium chloride. This cationic surfactant is a quaternary ammonium salt capable of inhibiting the growth of microorganisms in the novel topical exfoliating formulation.

In a preferred embodiment, the novel topical exfoliating formulation has about 0.001% papain enzyme obtained from the green papaya fruit. Papaya Extract is capable of separating or lysing cells, whereby, the extracellular matrix interrupts the connections between cells. Therefore, papaya extract of the novel topical exfoliating formulation facilitates removal of dead skin cells of a user's skin.

In a preferred embodiment, the novel topical exfoliating formulation has about 0.500% citrus seed extract. It is within the scope of this invention for the citrus seed extract to be grapefruit seed extract. Grapefruit seed extract is at least one of a nontoxic preservative in the novel topical exfoliating formulation.

In a preferred embodiment, the novel topical exfoliating formulation has about 0.500% preservative. It is within the scope of the current invention for the novel topical exfoliating formulation to have at least two preservatives. At least two preservatives of the novel topical exfoliating formulation are grapefruit seed extract and benzylalcohol DHA. Benzylalcohol DHA comprises benzylalcohol and dehydroacetic acid to inhibit growth of microbes including, but not limited to, bacteria, mold, yeast, and fungus within the novel topical exfoliating formulation.

In a preferred embodiment, the novel topical exfoliating formulation has about 0.001% to about 0.025% fragrance. It is within the scope of the current invention for the novel topical exfoliating formulation to have about 0.010% fragrance. The fragrance may include, but not be limited to, fragrance fruity floral N38090-WS.

In an alternate embodiment, the novel topical exfoliating formulation may be exposed to about 5 rads to about 10 rads of gamma radiation. It is within the scope of this invention for the gamma radiation process to occur either before, during, or after packaging of the product within an air tight vessel in an attempt to reduce or eliminate microorganisms from the novel topical exfoliating formulation.

The novel topical exfoliating formulation is retained in an air tight vessel including, but not limited to, a bottle, a jar, a bag, a syringe, or an airless pump syringe. It is within the scope of this invention for the air tight vessel to be any sterile dispenser capable of retaining the novel topical exfoliating formulation. A preferred embodiment of the sterile dispenser is an airless pump bottle or an airless pump syringe capable of protecting the novel topical exfoliating formulation by preventing excessive exposure to air and preventing exposure to a user's cross contamination, thus increasing product shelf life and protecting the formulation from harmful microorganisms associated with cross contamination by a user. The airless bottle or the airless syringe has no dip tube but rather a diaphragm that rises to evacuate the product, thus, a user does not come into contact with the entire reservoir retaining the novel topical exfoliating formulation. When user depresses the pump, it creates a vacuum effect, drawing the product upwards. A user can use almost all of the products without any waste left over and the problem of standard pumps not working appropriately is eliminated.

It will thus be seen that the objects set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

The invention claimed is:
1. An aqueous formulation for topical chemical exfoliation to the skin, comprising, by weight:
about 80.000% to about 90.000% water;
about 3.000% to about 4.000% polyacrylic acid;

about 0.025% to about 0.100% disodium ethylenediaminetetraacetate;
about 0.250% to about 1.000% glycerin;
about 3.000% to about 5.000% specially denatured alcohol;
about 0.025% to about 0.100% dimethicone;
about 4.000% to about 6.000% cetyltrimethylammonium chloride;
about 0.0001% to about 0.025% papain enzyme;
about 0.025% to about 1.000% citrus seed extract; and,
about 0.025% to about 1.000% preservative.

2. The formulation of claim 1, wherein the formulation comprises about 86.139% water.

3. The formulation of claim 1, wherein said polyacrylic acid is crosslinked with an allyl ether of pentaerythritol.

4. The formulation of claim 1, wherein said polyacrylic acid is crosslinked with an allyl ether of sucrose.

5. The formulation of claim 1, wherein said polyacrylic acid is crosslinked with an allyl ether of propylene.

6. The formulation of claim 1, wherein the formulation comprises about 3.250% polyacrylic acid.

7. The formulation of claim 1, wherein the formulation comprises about 0.050% disodium ethylenediaminetetraacetate chelating agent.

8. The formulation of claim 1, wherein the formulation comprises about 0.500% glycerin.

9. The formulation of claim 1, wherein said specially denatured alcohol is denatured with tert-Butyl alcohol.

10. The formulation of claim 1, wherein the formulation comprises about 4.000% specially denatured alcohol.

11. The formulation of claim 1, wherein the formulation comprises about 0.050% dimethicone.

12. The formulation of claim 1, wherein the formulation comprises about 5.000% cetyltrimethylammonium chloride.

13. The formulation of claim 1, wherein the formulation comprises about 0.001% papain enzyme.

14. The formulation of claim 1, wherein the formulation comprises about 0.500% citrus seed extract.

15. The formulation of claim 1, wherein said citrus seed extract is grapefruit seed extract.

16. The formulation of claim 1, wherein the formulation comprises about 0.500% preservative.

17. The formulation of claim 1, wherein said preservative comprising benzylalcohol and dehydroacetic acid.

18. The formulation of claim 1, wherein the formulation comprises about 0.001% to about 0.025% fragrance.

19. The formulation of claim 18, wherein the formulation comprises about 0.010% fragrance.

20. The formulation of claim 1, wherein the formulation is retained in an air tight vessel.

21. The formulation of claim 20, wherein said air tight vessel having an airless pump mechanism.

22. The formulation of claim 21, wherein said air tight vessel is a syringe.

23. A method for reducing or eliminating microorganisms from the aqueous formulation according to claim 1, comprising applying about 5 rads to about 10 rads of gamma radiation to the formulation of claim 1.

24. A method for reducing or eliminating microorganisms from the aqueous formulation according to claim 20, comprising applying about 5 rads to about 10 rads of gamma radiation to the formulation of claim 20.

* * * * *